(12) United States Patent
Voytilla

(10) Patent No.: US 10,737,034 B2
(45) Date of Patent: Aug. 11, 2020

(54) METHOD OF MANUFACTURING A SEALING ELEMENT

(71) Applicant: PRECISION POLYMER PRODUCTS, INC., Pottstown, PA (US)

(72) Inventor: Joseph M. Voytilla, Pottstown, PA (US)

(73) Assignee: Precision Polymer Products, Inc., Pottstown, PA (US)

( * ) Notice: Subject to any disclaimer, the term of this patent is extended or adjusted under 35 U.S.C. 154(b) by 0 days.

(21) Appl. No.: 16/058,486

(22) Filed: Aug. 8, 2018

(65) Prior Publication Data

US 2018/0344940 A1 Dec. 6, 2018

Related U.S. Application Data

(62) Division of application No. 15/606,639, filed on May 26, 2017, now Pat. No. 10,058,658.

(51) Int. Cl.
| | |
|---|---|
| *B29C 45/14* | (2006.01) |
| *A61M 5/315* | (2006.01) |
| *A61M 5/50* | (2006.01) |
| *B65D 35/30* | (2006.01) |

(52) U.S. Cl.
CPC .... *A61M 5/31513* (2013.01); *A61M 5/31511* (2013.01); *A61M 5/31515* (2013.01); *A61M 5/50* (2013.01); *B29C 45/14* (2013.01); *A61M 2005/31521* (2013.01); *A61M 2207/00* (2013.01); *B65D 35/30* (2013.01)

(58) Field of Classification Search
None
See application file for complete search history.

(56) References Cited

U.S. PATENT DOCUMENTS

| | | | |
|---|---|---|---|
| 1,687,091 A | 10/1928 | Hein | |
| 3,150,801 A * | 9/1964 | Hamilton | A61M 5/31513 222/158 |

(Continued)

FOREIGN PATENT DOCUMENTS

| | | |
|---|---|---|
| JP | 2002327467 A | 11/2002 |
| JP | 2004162761 A1 | 6/2004 |

OTHER PUBLICATIONS

International Search Report and Written Opinion From related International Application No. PCT/US2018/034913 dated Oct. 24, 2018.

(Continued)

*Primary Examiner* — Edmund H Lee
(74) *Attorney, Agent, or Firm* — Howard IP Law Group, PC

(57) ABSTRACT

A method of manufacturing a sealing element for use in a fluid conveyance device comprising the steps of: forming an elastomeric sealing body including a first body portion defining at least one annular sealing rib, and a second body portion arranged on an end of the first body portion, the second body portion comprising an annular protrusion extending radially beyond the first body portion; and forming a layer of barrier material on a free end of the second body portion, wherein the forming steps are carried out in a single molding operation.

20 Claims, 11 Drawing Sheets

(56) References Cited

U.S. PATENT DOCUMENTS

| | | | | |
|---|---|---|---|---|
| 3,766,918 A | * | 10/1973 | Kessel | A61M 5/31511 604/125 |
| 4,363,329 A | * | 12/1982 | Raitto | A61M 5/3129 600/578 |
| 4,389,271 A | | 6/1983 | Shandy et al. | |
| 4,398,989 A | * | 8/1983 | Allen | B29C 31/066 156/245 |
| 4,846,031 A | | 7/1989 | Voytilla et al. | |
| 5,009,646 A | * | 4/1991 | Sudo | A61M 5/31513 604/230 |
| 5,120,148 A | | 6/1992 | Waters et al. | |
| 5,484,566 A | * | 1/1996 | Gabbard | B29C 43/146 264/250 |
| 6,004,300 A | * | 12/1999 | Butcher | A61M 5/31511 604/218 |
| 6,090,081 A | * | 7/2000 | Sudo | A61M 5/31513 604/218 |
| 6,165,402 A | * | 12/2000 | Gabbard | B29C 43/021 264/255 |
| 7,927,315 B2 | * | 4/2011 | Sudo | A61M 5/31511 604/218 |
| 8,641,416 B2 | * | 2/2014 | Leiner | A61M 5/3148 433/90 |
| 8,722,178 B2 | * | 5/2014 | Ashmead | A61M 5/31513 428/212 |
| 9,067,346 B2 | * | 6/2015 | Kohn | B29C 45/0055 |
| 2003/0035744 A1 | * | 2/2003 | Horita | A61M 5/3135 417/460 |
| 2004/0099994 A1 | | 5/2004 | Brinkhues | |
| 2009/0047622 A1 | | 2/2009 | Leiner et al. | |
| 2016/0193418 A1 | | 7/2016 | Kubo | |
| 2016/0243308 A1 | * | 8/2016 | Giraud | A61M 5/31513 |

OTHER PUBLICATIONS

Dounce, "The Evolution of Fluoropolymer Coatings for Parenteral Packaging". Datwlyer Sealing Solutions. www.ondrugdelivery.com, 2015 (This date is sufficiently earlier than the effective U.S. filing date of the instant application.).

Roessling et al., "Prefilled Syringes: Innovations that Meet the Growing Demand". ONdrugDELIVERY. www.ondrugdelivery.com, 2005 (This date is sufficiently earlier than the effective U.S. filing date of the instant application.)

"What's the Difference Between a Teflon Film-Coated and a FluroTec Film-Coated Stopper?" West Pharmaceutical Services. Customer Service Blog, Jan. 30, 2014.

* cited by examiner

METHOD OF MANUFACTURING A SEALING ELEMENT

CROSS REFERENCE TO RELATED APPLICATIONS

This application is a divisional of and claims priority benefit under 35 USC 120 to U.S. patent application Ser. No. 15/606,639, filed on May 26, 2017, now U.S. Pat. No. 10,058,658, the subject matter of which is hereby incorporated by reference in its entirety.

FIELD OF THE INVENTION

The present invention relates generally to molded sealing articles, and more specifically, to methods and systems of manufacturing molded plungers and stoppers having a barrier film attached thereto.

BACKGROUND

Syringes are often used to deliver fluids (i.e. liquids and gases). These devices generally comprise a reciprocating pump utilizing a plunger or piston fitted within a cylindrical body or barrel. As the plunger is biased within the barrel, fluid may be drawn into the barrel or expelled therefrom. An open end of a syringe may be fitted with a needle, nozzle, or other interface depending on a desired application. Syringes are frequently used in clinical medicine to administer injections, infuse intravenous pharmaceutical products into the bloodstream, apply compounds such as glue or lubricant, and to draw and measure liquids. Stoppers or caps are widely used in many industries, including the medical industry, for selectively sealing or closing containers such as vials.

Pharmaceutical products or solutions often have characteristics that present an increased likelihood of unwanted interaction between the product and certain types of materials. For example, polymer materials, such as rubber used to make plungers used in syringe assemblies and stoppers used to close medical containers, are subject to leakage or chemical breakdown which can contaminate the solution. In order to prevent these chemical reactions between the polymer material and the solution, chemically inert barrier layers or films, such as those formed from fluoropolymer materials, are provided on surfaces of the components that will be exposed to the solution.

Particularly in the field of syringe plungers, the addition of this barrier material or layer complicates the manufacturing process. Moreover, in order to create a reliable barrier, plunger designs have required relatively thick barrier material layers. These drawbacks significantly increase manufacturing costs. More specifically, and referring generally to FIG. 1, an exemplary plunger 2 of the prior art is shown. Plunger 2 comprises a first end or face 3 which is exposed to a substance (e.g., fluid or solution) when installed within a syringe. Plunger 2 terminates at a second end 7 configured to attach to, for example, a moveable plunger rod for selectively biasing plunger 2 within a barrel of the syringe. In order to isolate the body of plunger 2 from a solution contained within a syringe, a barrier layer or barrier film must be formed over face 3. In order to ensure complete isolation between the body of plunger 2 and the solution, this layer must be applied over a first sealing rib 8 and up to or beyond a point of tangency or contact T with an internal barrel wall of a syringe. In order to reliably form this layer around at least a portion of sealing rib 8, a two-step over molding process for manufacturing plunger 2 is typically employed. In a first step, a first portion 4 of plunger 2 is molded and a barrier material subsequently formed over face 3, as well as at least a portion of sealing rib 8. Forming the barrier layer over the radiuses of sealing rib 8 commonly leads to the formation of undesirable wrinkles and/or tears in the layer that may result in capillary fissures. Moreover, ensuring uninterrupted and uniform coverage of this layer typically requires a relatively thick (e.g., five thousands of an inch), and therefore more expensive, layer of barrier material. Once formed, a second portion 6 of plunger 2 is molded over and joined with first portion 4, creating a monolithic body. This two-step process is time consuming and expensive. Many of the above drawbacks also apply to stoppers or sealing devices which utilize barrier layers or films.

Alternative designs and manufacturing processes for these items are desired.

SUMMARY

According to an embodiment of the present disclosure, a sealing article for use in a fluid conveyance device, such as a syringe or vial, is provided. The sealing article includes a body defining an annular protrusion of a first diameter extending radially outward from a first end thereof. The annular protrusion defines a radial lip that overhangs a portion of the body directly adjacent thereto. The sealing article further includes a layer of barrier material attached (e.g. bonded) to the first end of the body and covering a portion of the annular protrusion.

According to another embodiment of the present disclosure, a sealing article for use in a fluid conveyance device comprises an elastomeric body including a first end defining a disk-shaped annular protrusion, and an annular recess formed in a sidewall thereof directly adjacent the first end of the body in an axial direction of the body. The annular recess is sized to receive at least a portion of the annular protrusion. A barrier material is attached to a first end of the body and extends over the radial protrusion.

A method of manufacturing a sealing article for use in a fluid conveyance device according to an embodiment of the present disclosure comprises the steps of forming a body including a first body portion defining at least one annular sealing rib, and a second body portion arranged on an end of the first body portion. The second body portion comprises an annular protrusion extending radially beyond the first body portion. A layer of barrier material is applied to a free end of the second body portion.

A syringe assembly according to another embodiment of the present disclosure includes a barrel defining an interior cavity, and an elastomeric plunger. The plunger includes a first end defining a disk-shaped annular protrusion, and an annular recess formed in a sidewall thereof directly adjacent the first end of the body in an axial direction of the body and sized to receive at least a portion of the annular protrusion. A barrier material is attached to or formed on a first end of the elastomeric plunger and extends over the radial protrusion.

A method of manufacturing a syringe is provided. The method includes forming a plunger body including forming a first body portion defining at least one annular sealing rib, and forming a second body portion arranged on an end of the first body portion. The second body portion comprises an annular protrusion extending radially beyond the first body portion. A layer of barrier material is formed on or attached to a free end of the second body portion. The plunger body is inserted into a barrel of the syringe, wherein the annular protrusion is deflected in an axial direction and a radially-inward direction in response to the plunger being inserted into an interior cavity of the barrel.

A method of manufacturing a sealing element for use in a fluid conveyance device comprises the steps of: forming an elastomeric sealing body including a first body portion defining at least one annular sealing rib, and a second body portion arranged on an end of the first body portion, the second body portion comprising an annular protrusion extending radially beyond the first body portion; and forming a layer of barrier material on a free end of the second body portion, wherein the forming steps are carried out in a single molding operation.

DETAILED DESCRIPTION

Figure 1:
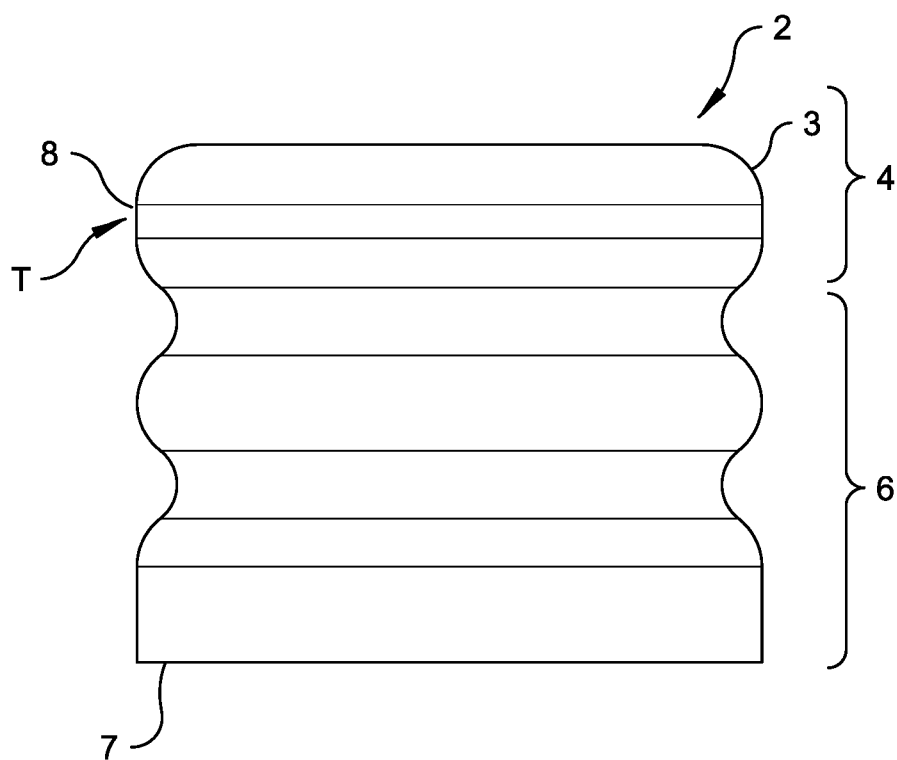
FIG. 1 is a perspective view of a plunger or piston for use in a syringe or other fluid conveyance device according to the prior art.

It is to be understood that the figures and descriptions of the present invention have been simplified to illustrate elements that are relevant for a clear understanding of the present invention, while eliminating, for purposes of clarity, many other features found in fluid delivery systems, such syringes, as well as polymer molding processes. However, because such elements and processes are well known in the art, and because they do not facilitate a better understanding of the present invention, a discussion of such elements is not provided herein. The disclosure herein is directed to all such variations and modifications known to those skilled in the art.

In the following detailed description, reference is made to the accompanying drawings that show, by way of illustration, specific embodiments in which the inventions may be practiced. It is to be understood that the various embodiments of the inventions, although different, are not necessarily mutually exclusive. Furthermore, a particular feature, structure, or characteristic described herein in connection with one embodiment may be implemented within other embodiments without departing from the scope of the inventions. In addition, it is to be understood that the location or arrangement of individual elements within each disclosed embodiment may be modified without departing from the scope of the inventions. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout several views.

Embodiments of the present disclosure include improved molded sealing articles, including plungers and stoppers or other sealing devices, such as those used in medical syringe assemblies and other pharmaceutical delivery or conveyance devices, and methods of manufacture thereof. Both plungers and stoppers may be described herein as sealing articles or sealing elements. As described above, prior art plungers which include barrier materials to protect pharmaceutical products from chemical leakage or other contamination are manufactured in a multi-step molding operation. Plungers according to embodiments of the present disclosure comprise a unique structure and profile, enabling their production in a single step molding process.

Specifically, a plunger according to one embodiment of the present disclosure includes a body including a main body portion having a maximum outer diameter defined by an exterior surface thereof, such as by one or more annular sealing ribs formed radially about the body. The exterior surface of the main body portion is configured (e.g. sized and shaped) to interface with an interior wall of, for example, a pharmaceutical product-containing cavity or barrel of a syringe. On a first end of the main body portion, a secondary body portion is provided. The secondary body portion comprises a generally cylindrical or disk-shaped profile and includes an annular, radially-extending protrusion. The secondary body portion including the protrusion comprises a diameter that is greater than that of the outer diameter of the main body portion. In this way, the protrusion extends beyond the main body portion in the radial direction, creating an overhanging body section or lip relative to the main body. A barrier material, such as a fluoropolymer film, is bonded or otherwise attached to an exposed planar end surface of the secondary body portion. The barrier material may comprise a similar circular or disk-shaped profile to that of the secondary body portion, and may substantially cover all of the exposed end surface thereof. The diameter of the secondary body portion may be sized so as to be greater than the inner diameter of an interior wall or inner cavity of a pharmaceutical solution-containing barrel of a syringe, by way of example.

In one particularly advantageous embodiment, the main body portion of the plunger further comprises an annular recess or notch formed in an outer surface thereof at a location directly adjacent the protrusion of the secondary body portion. This annular recess may be formed in a first sealing rib nearest an end of the main body portion. The annular recess is sized so as to accept at least a portion of the overhanging protrusion therein after it has been biased both axially in a direction toward a second end of the body, and radially inward toward a center of the body. The protrusion is sized so as to be biased in the described manner in response to its insertion into a barrel of a syringe. Once inserted, the secondary body portion, including the barrier material, extends in an axial direction at least a point of tangency with an exterior surface of the main body portion. In this way, after insertion into the syringe, the main body of the plunger is isolated from the contents of the syringe by the secondary body portion and the barrier material applied thereto. As will be set forth in greater detail herein, plungers according to embodiments of the present disclosure may be formed via single-step molding processes and may reliably implement relatively thin barrier layers, as distinct from plungers of the prior art.

Figure 2A:
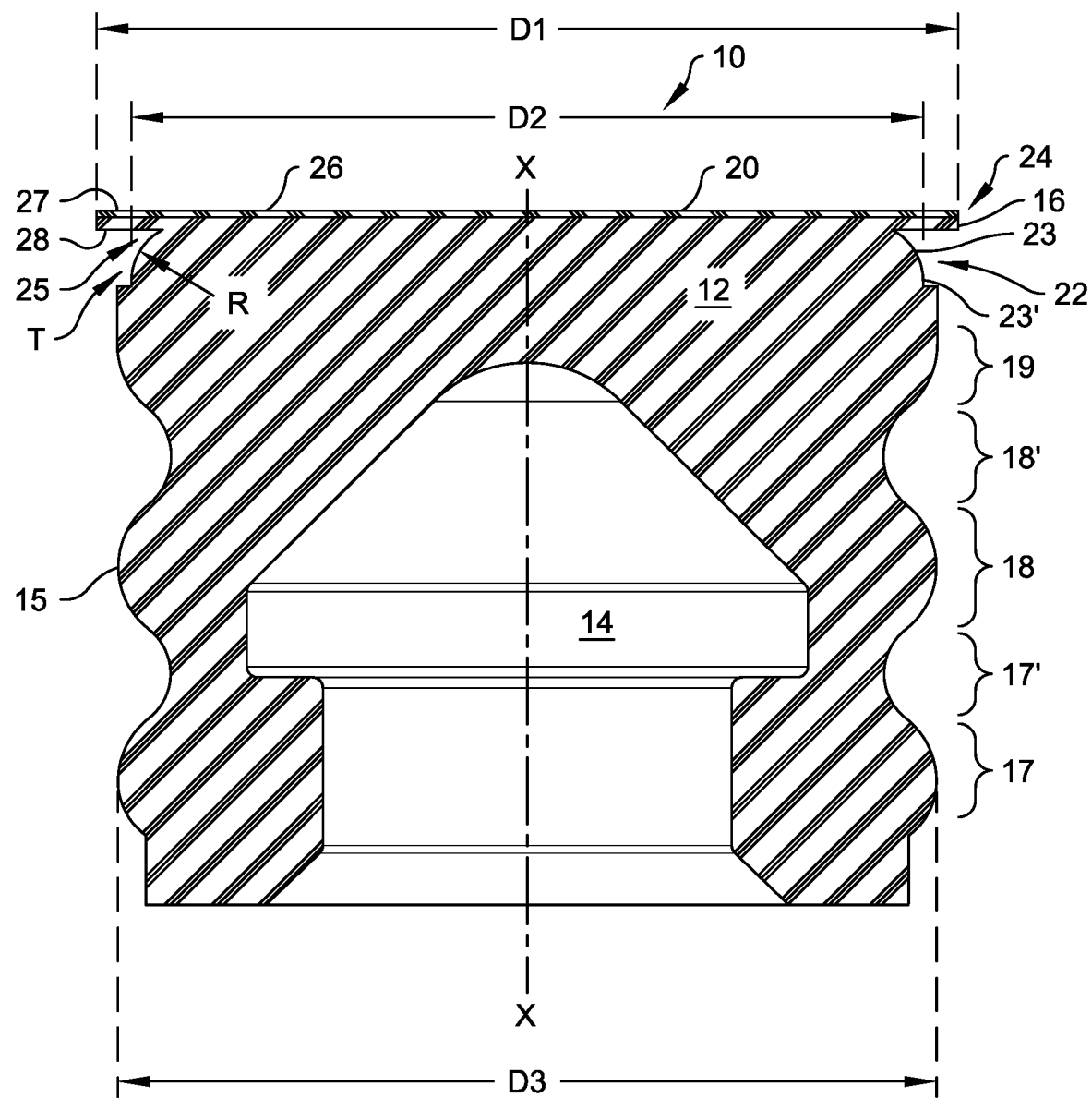
FIG. 2A is a cross-sectional view of a piston or plunger sealing article according to embodiments of the present disclosure.
Figure 2B:
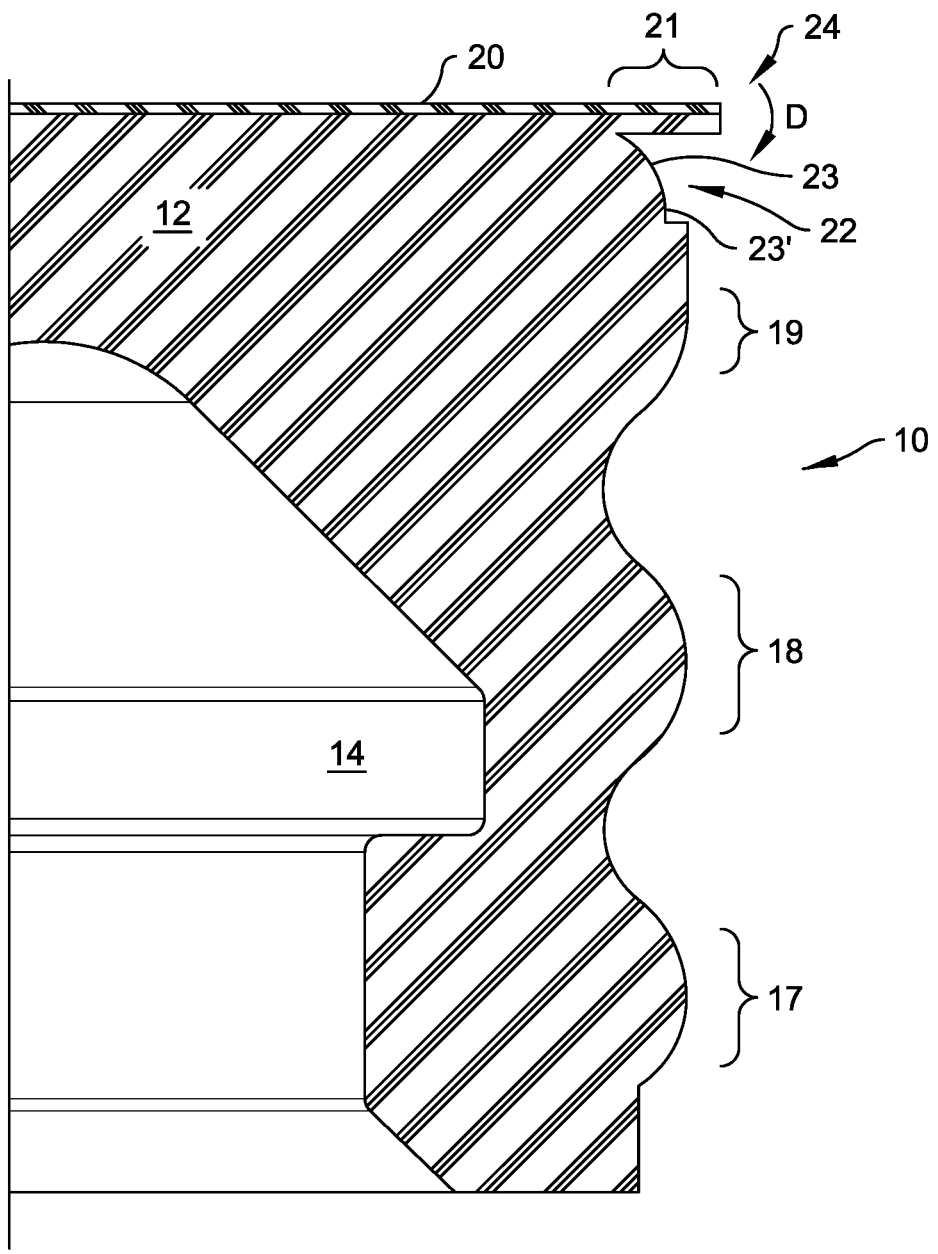
FIG. 2B is a cross-sectional view of a portion of the plunger sealing article of FIG. 2A.
Figure 2C:
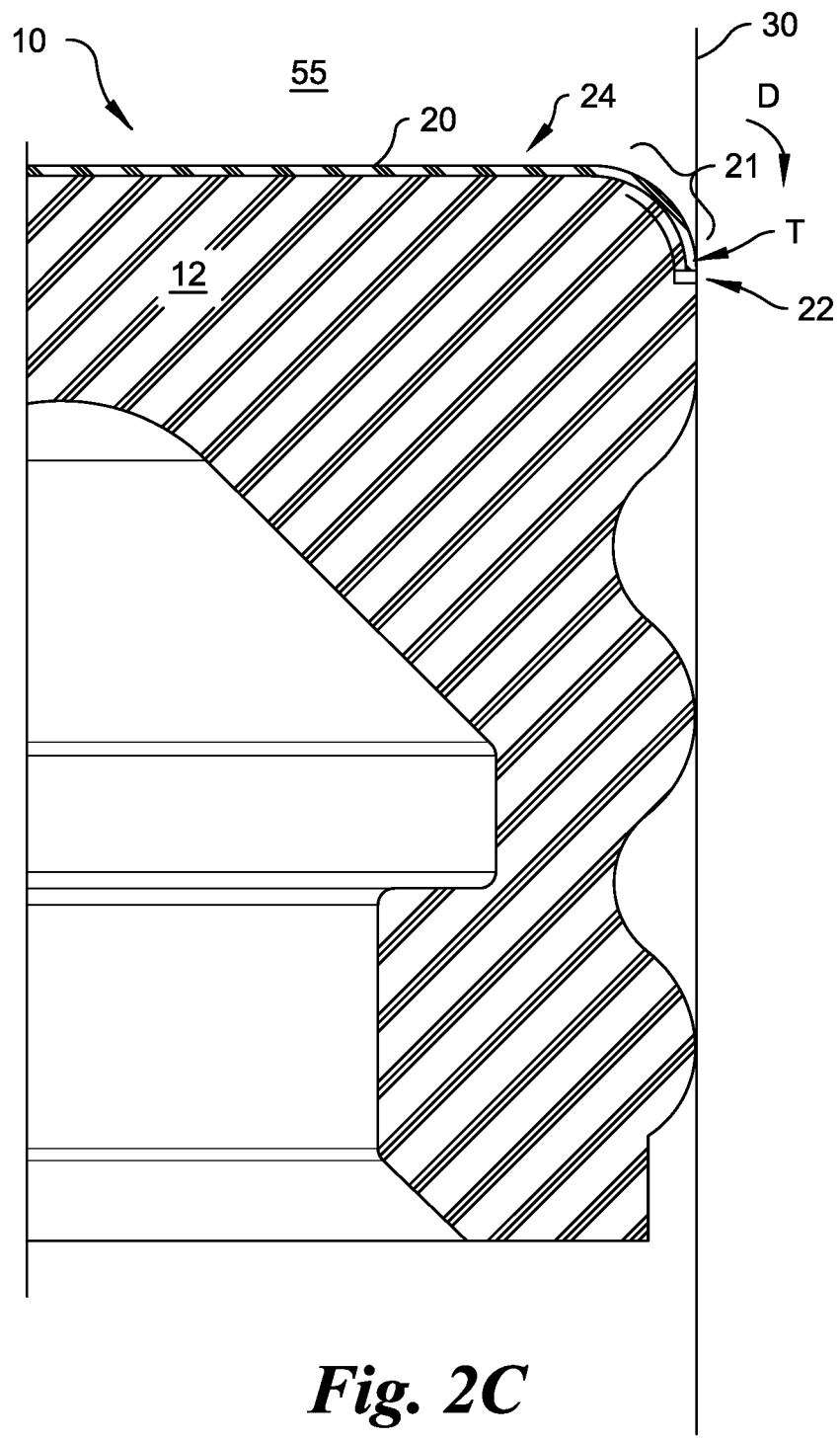
FIG. 2C is a cross-sectional view of the portion of the plunger sealing article of FIG. 2B, wherein a sealing lip has been biased into a position indicative of the plunger sealing article being inserted into a barrel of a syringe.

FIGS. 2A, 2B and 2C are cross-sectional views of a piston or plunger 10 for use in a solution delivery device according to embodiments of the present disclosure. Exemplary plunger 10 includes a main body or body portion 12. Body 12 may be made of a molded polymer material and defines an aperture 14 formed in an end thereof for interfacing with, and selectively attaching to (e.g., in a "snap-fit" manner), a correspondingly-sized end of a moveable plunger rod, as shown in FIGS. 3A and 3B. Plunger 10 may be defined with respect a central axis x about which body 12 may be symmetric. An outer or exterior surface 15 of body 12 defines a plurality of annular sealing protrusions or sealing ribs 17, 18, 19 formed radially about body 12 with respect to central axis x. Each rib 17, 18, 19 defines a generally convex exterior surface of body 12. Ribs 17, 18, 19 are separated by interposed radial concave surfaces 17', 18'. An outer diameter D3 of one or more sealing ribs 17, 18, 19 may be sized to be marginally greater than an inner diameter of an interior cavity or barrel of a syringe for enabling the formation of a seal therebetween after plunger 10 has been inserted therein. See, for example, diameter D4 in FIGS. 3A and 3B.

Still referring to FIGS. 2A, 2B and 2C, plunger 10 includes a secondary body portion or first end 24. Secondary body portion 24 may comprise a cylindrical or disk-shaped profile, including a generally planar end surface 26. Secondary body portion 24 defines a radially extending annular protrusion 16. Annular protrusion 16 extends beyond a portion of body 12 arranged immediately adjacent thereto, and in some embodiments, beyond a remainder of all portions of body 12 in the radial direction. In this way, protrusion 16 defines an overhanging portion or radial lip 21 (FIG. 2B). As illustrated, overhanging portion 21 is defined by two generally planar, parallel sidewalls 27, 28 extending radially from a remainder of body 12 in a direction generally perpendicular to central axis x. As shown, sidewall 27 partially defines the planar end surface 26, while the opposite sidewall 28 faces a second end of plunger 10. While overhanging portion 21 is shown as extending radially from a remainder of body 12 in a direction generally perpendicular to central axis x, it should be understood that overhanging portion 21 may extend, for example, in non-orthogonal direction with respect to central axis x.

Secondary body portion 24 including protrusion 16 may comprise a diameter D1 that is greater than a diameter of any other portion of body 12, including diameter D3 of sealing ribs 17, 18, 19. As will be set forth in greater detail herein, secondary body portion 24 including protrusion 16 may be formed monolithically with a remainder of body 12 during, for example, a single molding operation. A chemically inert barrier material or barrier film 20, such as a fluoropolymer film by way of non-limiting example, is bonded or otherwise attached to the exposed planar surface of secondary body portion 24. As barrier 20 material is bonded to planar end surface 26 of secondary body portion 24, as distinct from barrier materials formed about curved surfaces, the thickness of barrier material 20 can be significantly reduced (e.g., as low as 0.002 to 0.005 inches, while maintaining reliable sealing characteristics.

Exterior surface 15 of body 12 further defines, in an area directly adjacent secondary body portion 24, a recess or notch 22 formed, for example, at least partially in sealing rib 19 arranged nearest a first end of plunger 10. As illustrated, exemplary recess 22 comprises a first arcuate or radiused portion 23 forming a convex exterior curve of body 12 and a second recessed portion 23'. Radiused portion 23 extends generally from secondary body portion 24 to second recessed portion 23', which in turn extends in a generally axial direction of body 12. Radiused portion 23 and secondary body portion 24 are sized to define an annular undercut or undercut area 25 (FIG. 2A) between secondary body portion 24 and a remainder of body 12.

FIG. 2C illustrates a partial cross-sectional view of plunger 10 after its insertion into a barrel 55 of a syringe. As illustrated, recess 22 is sized to receive at least a portion overhanging portion 21 of secondary body portion 24 in response to an application of force placed thereon by an interior wall 30 of the syringe. This force biases, deflects or folds overhanging portion 21 in a direction D, and more specifically, generally axially toward a second end of body 12 and radially inward with respect to central axis x (FIG. 2A). Overhanging portion 21 of body 12 and/or recess 22 may be sized such that overhanging portion 21 including barrier material 20 extends at least up to or beyond a resulting point of tangency T between itself and interior wall 30 of the syringe into which plunger 10 has been inserted. Point of tangency T may occur generally at the transition between radiused portion 23 and second recessed portion 23' of recess 22. In this way, a seal is created between plunger 10 and interior wall 30, wherein an the exposed face of secondary body portion 24 is completely covered by barrier material 20, isolating plunger 10 from a pharmaceutical product arranged within cavity 55 of the syringe.

Figure 3:
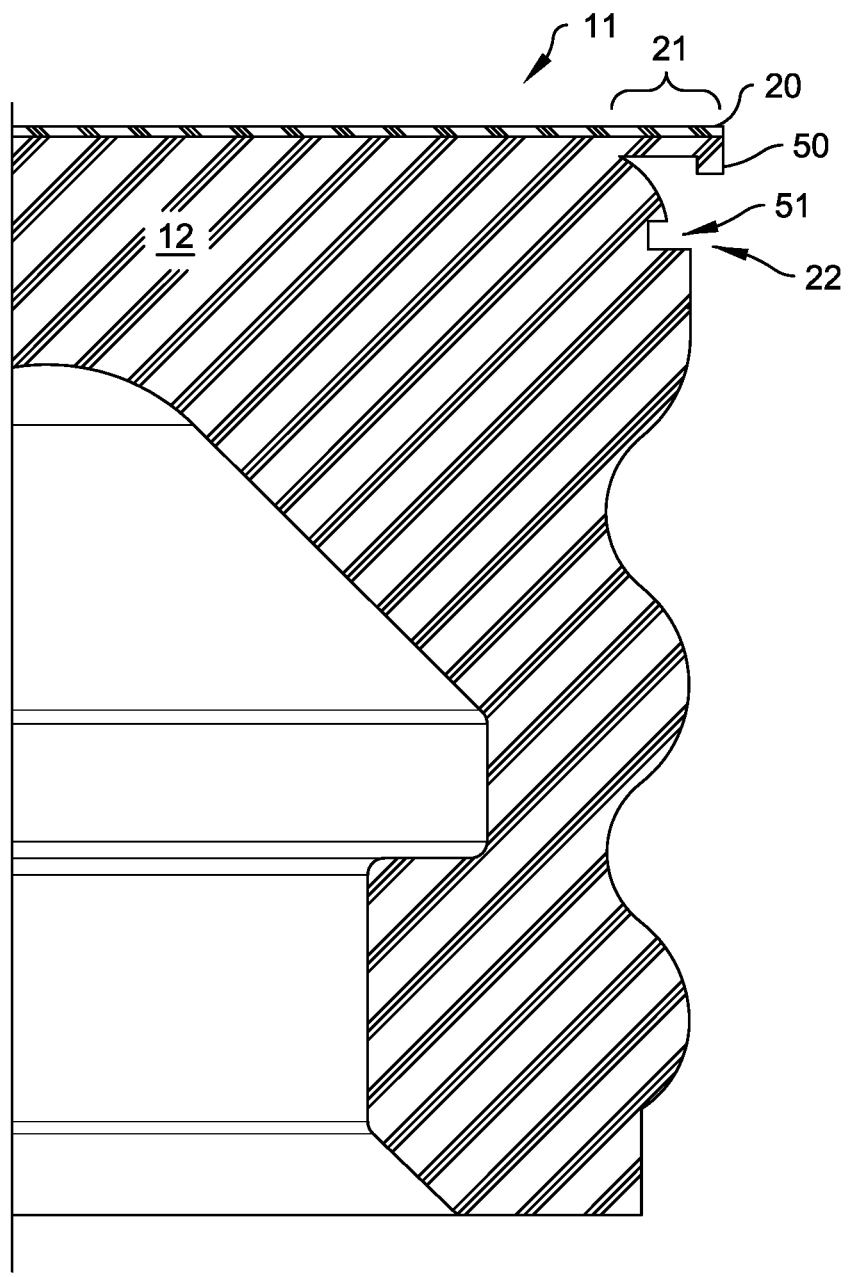
FIG. 3 is a cross-sectional view of a portion of a plunger sealing article according to another embodiment of the present disclosure.

FIG. 3 illustrates another embodiment of a plunger 11 according to the present disclosure. Plunger 11 comprises features similar to those set forth above with respect to FIGS. 2A-2C, including an overhanging portion 21 configured to be folded or biased generally into a recess 22 in response to its insertion into a barrel of a syringe, for example. Plunger 11 further comprises an additional retaining feature useful for maintaining the position of overhanging portion 21 within recess 22 in response to forces generated as plunger 11 is biased in axial directions within a syringe, for example. These forces may include friction forces generated between a sidewall of a syringe barrel and barrier film 20 in an area of overhanging portion 21. An exemplary retaining feature may be defined by an annular protrusion 50 extending from overhanging portion 21 and generally in an axial direction toward a second end of a body of plunger 11, and a complementary second annular recess 51 formed in, for example, an exterior surface of the plunger body defining recess 22. In response to plunger 11 being inserted into the barrel of a syringe or other device (see FIG. 2C), annular protrusion 50 will engage with second annular recess 51, wherein opposing surfaces thereof will secure overhanging portion 21 within recess 22. While this retaining feature has been described as utilizing an annular protrusion and a corresponding annular recess, embodiments of the present disclosure further include a plurality of discrete complementary protrusions and recesses formed radially around the body of a plunger (i.e., not in a continuous, annular manner).

Figure 4:
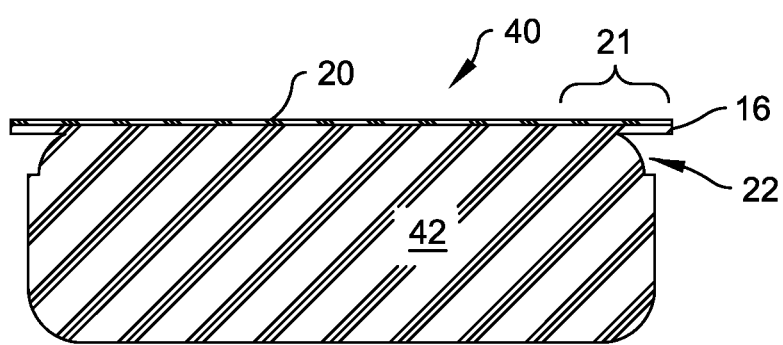
FIG. 4 is a cross-sectional view of a stopper sealing article according to an embodiment of the present disclosure having features similar to those set forth above with respect to the piston or plunger sealing article of FIGS. 2A, 2B and 2C.

Referring generally to FIG. 4, embodiments of the present disclosure further include stoppers, or other caps or lids, configured to be at least partially inserted into a fluid container for sealing its contents therein. Exemplary stopper 40 includes a body 42 sized to be at least partially inserted into a container or fluid conveyance device, such as a vial. Stopper 40 includes features similar to those set forth above with respect to FIGS. 2A-2C, with like-numerals representing like-features. Specifically, body 42 of stopper 40 defines a radially-extending annular protrusion 16 formed on an end thereof defining an overhanging portion 21. A barrier material or film 20 is attached to an end of body 42, and generally extends over a surface of overhanging portion 21. Upon insertion into a container, overhanging portion 21 including barrier material 20 is biased into a corresponding recess 22 for forming a seal between body 42 and an interior cavity of the container, as described above with respect to FIG. 2C.

Figure 5A:
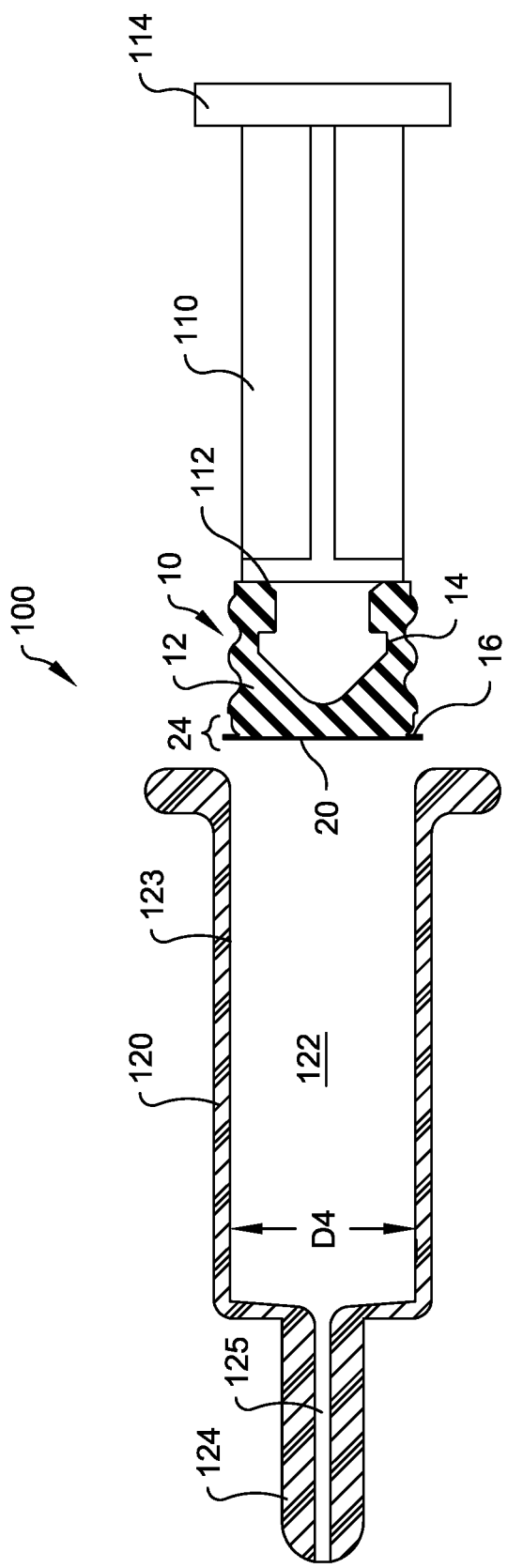
FIG. 5A is cross-sectional view of a syringe assembly in an unassembled state utilizing the plunger sealing article of FIGS. 2A, 2B and 2C.

FIG. 5A is cross-sectional view of an exemplary syringe assembly 100 utilizing plunger 10 according to the embodiments of FIGS. 2A-2C in an unassembled state. Syringe 100 comprises a main body or barrel 120 defining a cavity space 122 for holding a solution, such as a liquid pharmaceutical product. Cavity space 122 comprises an internal diameter D4 defined by an interior wall 123. Body 120 further defines a first end 124 having a channel or aperture 125 formed therethrough in communication with cavity space 122. While not shown, end 124 may be embodied as a needle, a nozzle or a tube, for example, depending on the application of syringe 100, as would be understood by one of ordinary skill in the art. Syringe 100 further comprises a plunger rod 110 defining an end surface 114, such as a planar surface for enabling the application of force on the plunger rod by, for example, a hand of a user. Plunger rod 110 further defines a plunger interfacing portion, embodied as a protruding surface 112 for attaching (e.g., in a snap-fit manner) plunger rod to plunger 10.

Figure 5B:
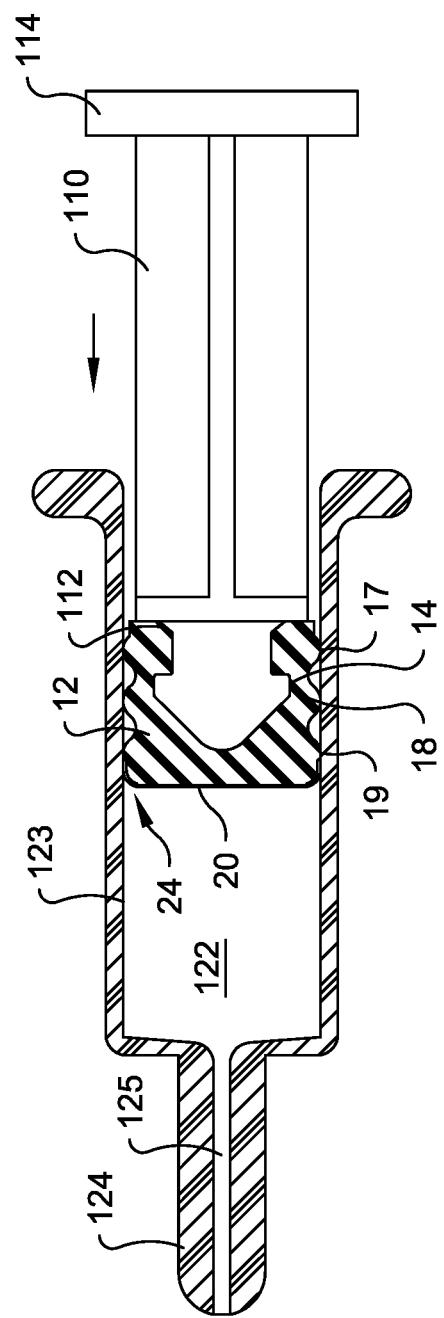
FIG. 5B is a cross-sectional view of the syringe assembly of FIG. 5A in an assembled state.

FIG. 5B is a cross-sectional view of syringe assembly 100 of FIG. 5A in an assembled state, wherein plunger 10 has been inserted into cavity space 122. As shown, protrusion 16 (FIG. 4A) of secondary body portion 24, including barrier material 20 has been folded or deflected axially and radially inward in response to the application of force placed thereon by interior wall 123 of syringe 100. As secondary body portion 24 and barrier material 20 extend to a point of contact with interior wall 123, a seal is created between plunger 10 and interior wall 123, thereby isolating plunger 10 from a pharmaceutical product arranged within cavity space 122 of syringe 100. In operation, as would be understood by one of ordinary skill in the art, a force applied in an axial direction of syringe 100 on end surface 114 of plunger rod 110 is operative to expel a solution contained within cavity 122 from syringe 100 via aperture 125. Pressure applied on the solution is generated via the force applied by the user in conjunction with a seal created between interior wall 123 of cavity 122 and sealing surfaces of plunger 10, such as the exemplary plurality of sealing ribs or 17, 18, 19 and secondary body portion 24.

Figure 6A:
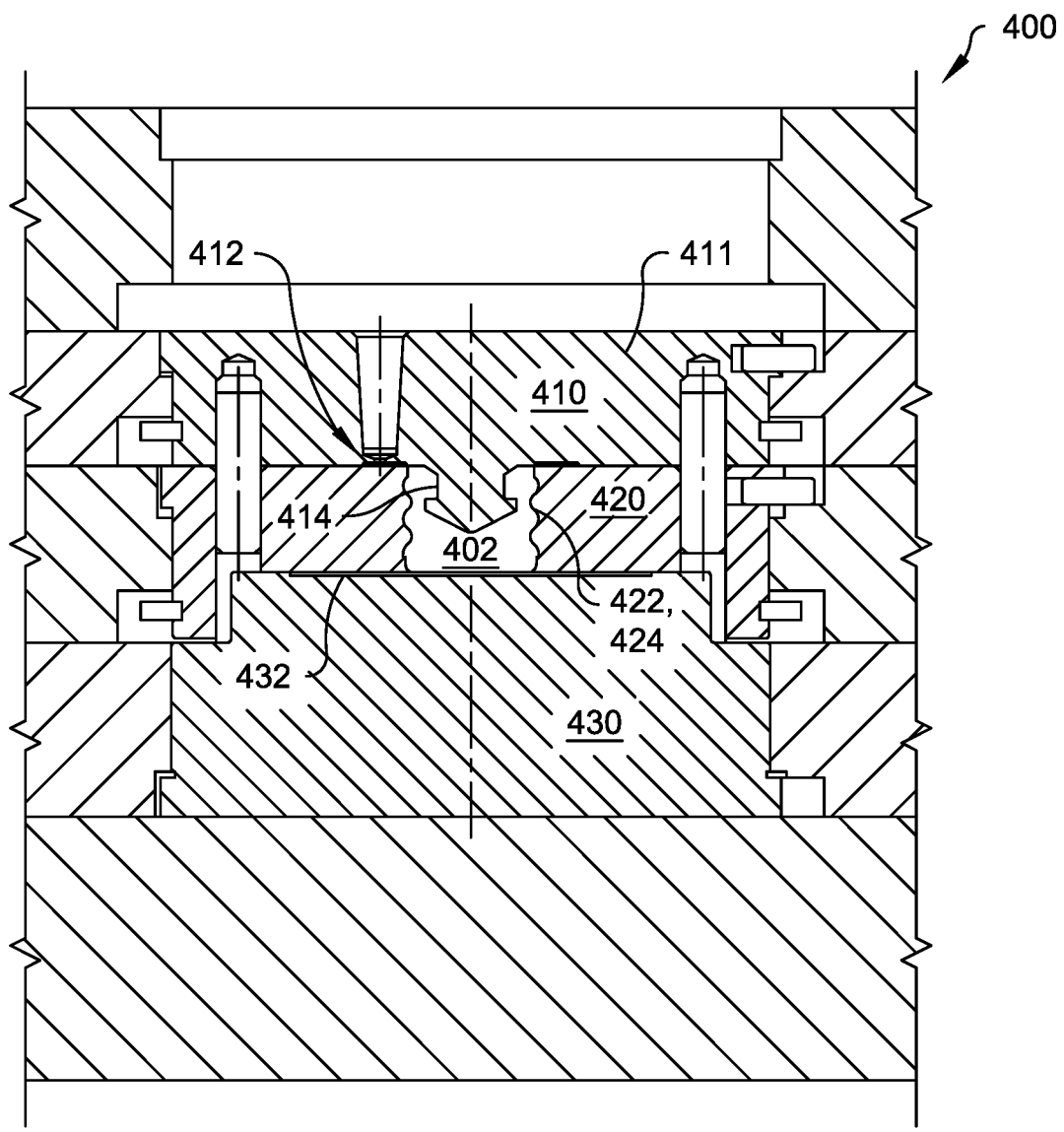
FIG. 6A is a cross-sectional view of an assembled three-insert mold useful for manufacturing plunger sealing articles according to embodiments of the present disclosure.
Figure 6B:
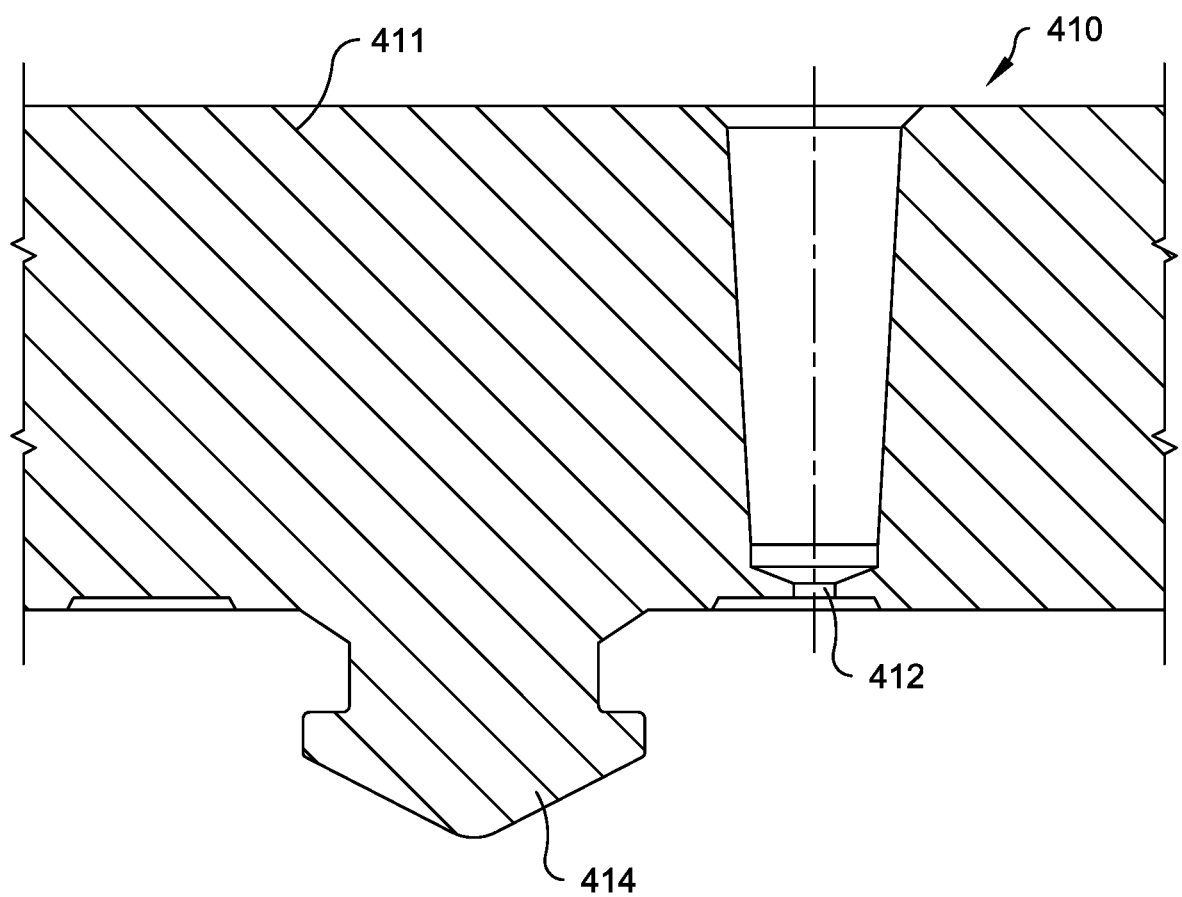
FIG. 6B is a cross-sectional view of a first insert of the assembled mold of FIG. 6A.
Figure 6C:
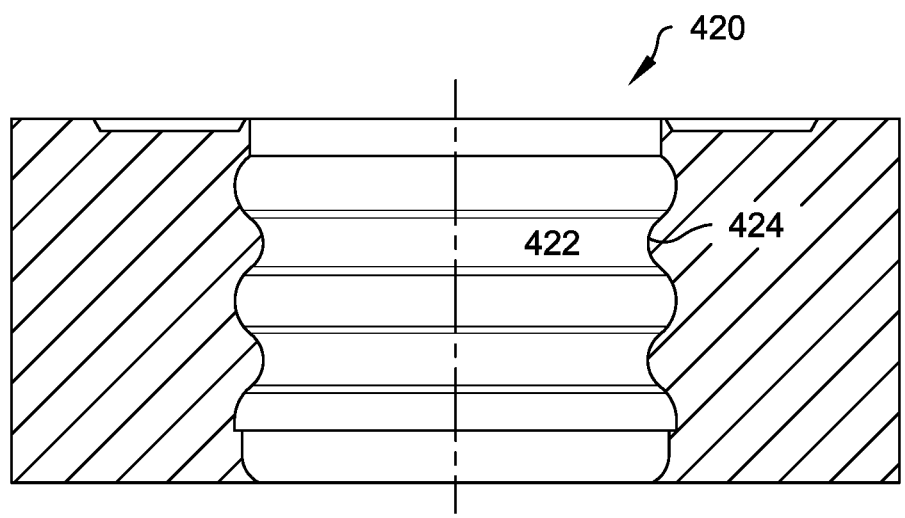
FIG. 6C is a cross-sectional view of a second insert of the assembled mold of FIG. 6A.
Figure 6D:
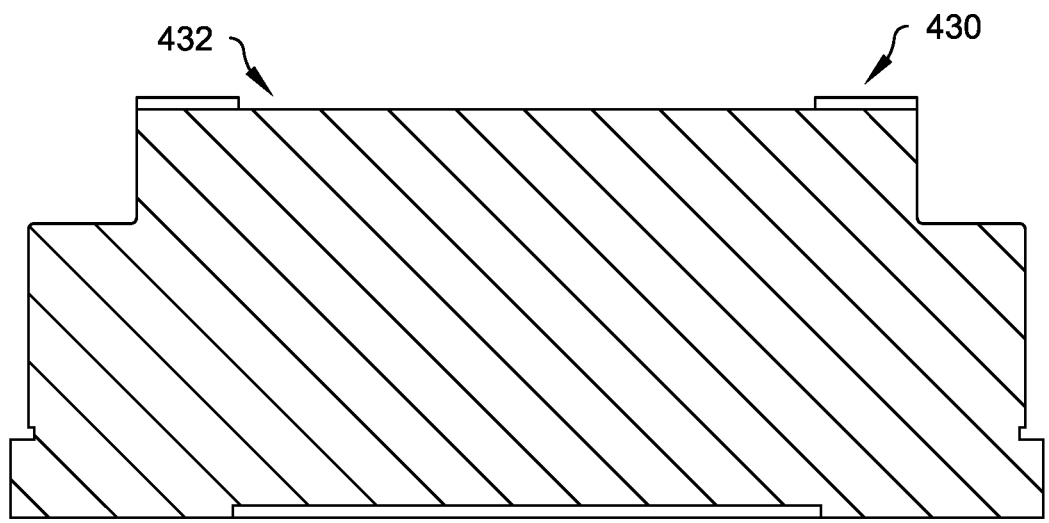
FIG. 6D is a cross-sectional view of a third insert of the assembled mold of FIG. 6A.

Referring generally to FIGS. 6A, 6B, 6C and 6D, an exemplary method of manufacturing a plunger 10 according to embodiments of the present disclosure will be described. As set forth above, plungers of the prior art that include barrier films applied over an end thereof must be manufactured with multi-step or overmolding processes. Embodiments of the present disclosure, however, may be manufactured in a single molding operation using, for example, the three-part mold illustrated in FIGS. 6A-6D. Specifically, FIG. 6A provides an assembled view of a three-insert mold used to manufacture plungers according to embodiments of the present disclosure. Mold assembly 400 includes an upper or top mold insert 410 (FIG. 6B), a middle or intermediate mold insert 420 (FIG. 6C), and a lower or bottom mold insert 430 (FIG. 6D). In the assembled state shown in FIG. 6A, mold inserts 410, 420, 430 define a hollow interior cavity 402 in which an plunger according to the embodiments of the present disclosure is formed. More specifically, top insert 410 includes a body 411 defining a sprue 412 for introducing material into cavity 402 via, for example, at least one runner and gate arrangement. Insert 410 further comprises a protrusion 414 for forming the aperture of the plunger (aperture 14 of FIGS. 2A-2C). As shown, when insert 410 is arranged over insert 420, protrusion 414 is arranged within an aperture 422 defined through insert 420. Aperture 422 is defined by an interior wall 424 of insert 420. Interior wall 424 is sized and shaped so as to define an exterior wall of a plunger body (i.e. external surface 15 of FIGS. 2A-2C) having features similar to those set forth above with respect to FIGS. 2A-2C.

The secondary, disk-shaped body portion of the plunger is formed via a recess 432 defined in lower insert 430. In an alternative arrangement, the recess may be formed in a bottom of insert 420. In order to bond the barrier material to the secondary body portion formed within recess 432, a layer of barrier film is arranged generally between lower insert 430 and middle insert 420 prior to the injection of polymer material into cavity 402. The barrier material or film may be plasma etched on a side exposed to interior cavity 402. Upon injection of polymer material into cavity 402, and subsequent cooling thereof, a mechanical bond may be formed between the etched side of the barrier film and the polymer material, securing the film to the formed plunger. Likewise, chemical or adhesive bonding may also be achieved between the plunger and the barrier material or film via, for example, the application of a primer onto the film prior to the injection of polymer material into cavity 402. Once molded, the inserts may be disassembled, and the plunger removed. Excess material forming the secondary portion 24 and/or the barrier film layer of the plunger, and/or sprue material may be mechanically removed by one or more trimming operations.

While a single cavity mold is shown, it should be understood that molds may comprise a plurality of cavities for forming a plurality of plungers in a single mold assembly. Likewise, while a single-step molding process is described, embodiments of the present disclosure may be formed from multi-step or overmolding processes. Moreover, while a barrier material or barrier film is described as being attached to a plunger body as a part of the molding processes of forming the plunger, it should be understood that in other embodiments of the present disclosure, the barrier film or material can be bonded to the plunger after it has been molded in a second, discrete step.

While the foregoing invention has been described with reference to the above-described embodiment, various modifications and changes can be made without departing from the spirit of the invention. Accordingly, all such modifications and changes are considered to be within the scope of the appended claims. Accordingly, the specification and the drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations of variations of various embodiments. Combinations of the above embodiments, and other embodiments not specifically described herein, will be apparent to those of skill in the art upon reviewing the above description.

What is claimed is:

1. A method of manufacturing a sealing element for use in a fluid conveyance device comprising the steps of:
    forming an elastomeric sealing body including a first body portion defining at least one annular sealing rib and an annular recess, and a second body portion arranged on an end of the first body portion, the second body portion comprising an annular protrusion adjacent to the annular recess and extending radially beyond the first body portion to define a radial lip, defined by two generally planar, parallel sidewalls, that overhangs the annular recess; and
    forming a layer of barrier material on a free end of the second body portion,
    wherein the forming steps are carried out in a single molding operation.

2. The method of claim 1, wherein the step of forming the layer of barrier material on a free end of the second body portion comprises bonding the barrier material to the free end of the second body portion.

3. The method of claim 1, wherein the free end of the second body portion comprises a planar surface, and wherein the planar surface includes the annular protrusion.

4. The method of claim 1, wherein the annular recess defines an annular undercut between the first body portion and the second body portion.

5. The method of claim 4, further comprising the steps of:
    inserting the elastomeric sealing body into an interior cavity of the fluid conveyance device, wherein the annular protrusion is deflected in an axial direction and a radially-inward direction in response to the elastomeric sealing body being inserted into the interior cavity of the fluid conveyance device.

6. The method of claim 5, wherein the elastomeric sealing body comprises a plunger, and wherein the fluid conveyance device comprises a syringe having a barrel into which the plunger is inserted.

7. The method of claim 1, wherein the step of forming an elastomeric sealing body including a first body portion defining at least one annular sealing rib and an annular recess, and a second body portion arranged on an end of the first body portion, the second body portion comprising an annular protrusion adjacent to the annular recess and extending radially beyond the first body portion to define the radial lip that overhangs the annular recess, wherein the annular recess is sized and located to receive at least a portion of the radial lip in response to a force biasing the annular protrusion toward the annular recess, comprises:
    providing an insert mold assembly having an interior cavity in which the elastomeric sealing body is formed, said interior cavity defining the first body portion having at least one annular sealing rib, and terminating at an annular recess of said insert mold assembly that defines an interior end of said insert mold assembly, wherein said annular recess extends radially outward from said interior cavity first body portion, to thereby define a radial lip cavity under the overhang defined by the radial lip; and
    providing a sprue through a portion of the insert mold assembly that engages with said cavity for introducing polymeric material into said cavity to form the elastomeric sealing body.

8. The method of claim 7, wherein the step of forming a layer of barrier material on a free end of the second body portion comprises:
    introducing a barrier material layer into said annular recess including said radial lip cavity of said insert mold assembly that defines the interior end portion of said insert mold assembly and is exposed to said interior cavity; and
    after said introducing step, injecting said polymeric material into said interior cavity via said sprue to fill the interior cavity and engage with the barrier material layer in said annular recess, thereby forming said sealing element.

9. The method of claim 8, further comprising plasma etching the barrier material layer on a side exposed to the interior cavity, prior to said injecting step.

10. The method of claim 8, further comprising applying a chemical or adhesive bonding primer onto the barrier material layer on a side exposed to the interior cavity, prior to said injecting step.

11. The method of claim 8, wherein the interior cavity annular sealing rib has a first arcuate convex surface extending from the interior end up to a first discontinuous position, wherein at the first discontinuous position the width of the interior cavity is at a maximum, and whose width decreases relative to said first discontinuous position distal from the interior end along said interior cavity annular sealing rib, thereby defining an undercut; and
    wherein upon removal from said mold assembly, trimming said layer of barrier material and free end of the second body portion so that the free end and barrier layer covering the free end is fully received in the undercut of the second body portion in response to a force biasing the free end toward the undercut of the second body portion.

12. A method of forming a sealing element in a single molding process comprising:
    providing an insert mold assembly having an interior cavity in which the sealing element is formed, said interior cavity defining a first body portion having at least one annular sealing rib, and terminating at an annular recess of said insert mold assembly that defines an interior end of said insert mold assembly, wherein said annular recess extends radially outward from said interior cavity first body portion, to thereby define a radial lip, defined by two generally planar, parallel sidewalls, and a radial lip cavity;

introducing a barrier material layer into said annular recess including said radial lip cavity of said insert mold assembly that defines the interior end portion of said insert mold assembly; and after said introducing step, injecting polymeric material into said interior cavity to fill the interior cavity and engage with the barrier material layer in said annular recess, thereby forming said sealing element.

13. The method of claim 12, wherein the interior cavity annular sealing rib has a first arcuate convex surface extending from the interior end up to a first discontinuous position, wherein at the first discontinuous position the width of the interior cavity is at a maximum, and whose width decreases relative to said first discontinuous position distal from the interior end along said interior cavity annular sealing rib, thereby defining an undercut for receiving the free end of the radial lip when the radial lip is biased in a direction toward the undercut.

14. The method of claim 13, wherein the step of providing an insert mold assembly comprises:
providing a first insert mold having a top surface and a bottom surface opposite said top surface, said first insert mold including a sprue for introducing polymeric material into said insert mold assembly;
providing a second insert mold having a top surface and a bottom surface opposite said top surface, said second insert mold having formed there through said interior cavity having at least one rib;
providing a third insert mold having a top surface and a bottom surface opposite the top surface;
assembling the first, second, and third insert molds in stacked engagement such that there is formed:
a passage from said sprue of said first insert mold to said cavity of said second insert mold for introducing polymeric material into said cavity; and
at an interface of said second insert mold and said third insert mold, the annular recess extending radially outward from said interior cavity.

15. The method of claim 14, further comprising providing a plunger shaped protrusion extending from a portion of the bottom surface of the first insert mold,
wherein the protrusion is configured so as to be accommodated within the interior cavity of the second insert mold upon stacked engagement thereof.

16. The method of claim 14, further comprising providing a recess along a portion of the top surface of said third insert mold; and engaging said top surface with the bottom surface of the second insert mold for forming the annular recess including the radial lip.

17. The method of claim 14, further comprising providing a recess along a portion of the bottom surface of said second insert mold; and engaging said bottom surface with the top surface of the third insert mold for forming the annular recess including the radial lip.

18. The method of claim 12, further comprising plasma etching the barrier material layer on a side exposed to the interior cavity, prior to said injecting step.

19. The method of claim 12, further comprising applying a chemical or adhesive bonding primer onto the barrier material layer on a side exposed to the interior cavity, prior to said injecting step.

20. A method of manufacturing a sealing element for use in a fluid conveyance device comprising the steps of:
forming an elastomeric sealing body including a first body portion defining at least one annular sealing rib, and a second body portion arranged on an end of the first body portion, the second body portion comprising an annular protrusion extending radially beyond the first body portion; and
forming a layer of barrier material on a free end of the second body portion,
wherein the forming steps are carried out in a single molding operation;
wherein the step of forming an elastomeric sealing body including a first body portion defining at least one annular sealing rib, and a second body portion arranged on an end of the first body portion, the second body portion comprising an annular protrusion extending radially beyond the first body portion, comprises:
providing an insert mold assembly having an interior cavity in which the elastomeric sealing body is formed, said interior cavity defining the first body portion having at least one annular sealing rib, and terminating at an annular recess of said insert mold assembly that defines an interior end of said insert mold assembly, wherein said annular recess extends radially outward from said interior cavity first body portion, to thereby define a radial lip cavity under the overhang of the annular protrusion; and
providing a sprue through a portion of the insert mold assembly that engages with said cavity for introducing polymeric material into said cavity to form the elastomeric sealing body;
wherein the step of forming a layer of barrier material on a free end of the second body portion comprises:
introducing a barrier material layer into said annular recess including said radial lip cavity of said insert mold assembly that defines the interior end portion of said insert mold assembly and is exposed to said interior cavity; and
after said introducing step, injecting said polymeric material into said interior cavity via said sprue to fill the interior cavity and engage with the barrier material layer in said annular recess, thereby forming said sealing element;
wherein the interior cavity annular sealing rib has a first arcuate convex surface extending from the interior end up to a first discontinuous position, wherein at the first discontinuous position the width of the interior cavity is at a maximum, and whose width decreases relative to said first discontinuous position distal from the interior end along said interior cavity annular sealing rib, thereby defining an undercut; and
wherein upon removal from said mold assembly, trimming said layer of barrier material and free end of the second body portion so that the free end and barrier layer covering the free end is fully received in the undercut of the second body portion in response to a force biasing the free end toward the undercut of the second body portion.

* * * * *